United States Patent
Goodman et al.

[11] Patent Number: 5,968,036
[45] Date of Patent: Oct. 19, 1999

[54] DENTAL PROCEDURES AND APPARATUS USING ULTRAVIOLET RADIATION

[75] Inventors: Barry Dean Goodman, Baldwin; James Jeffrey Wynne, Mount Kisco; Hershall William Kaufman, Setauket; Jason Matthew Jacobs, Baldwin, all of N.Y.

[73] Assignee: International Business Machines Corporation, Armonk, N.Y.

[21] Appl. No.: 09/057,304

[22] Filed: Apr. 8, 1998

Related U.S. Application Data

[62] Division of application No. 08/506,410, Jul. 24, 1995, Pat. No. 5,785,703, which is a division of application No. 08/271,385, Jul. 6, 1994, Pat. No. 5,435,724, which is a continuation of application No. 08/026,333, Mar. 4, 1993, abandoned.

[51] Int. Cl.$^6$ ..................................... A61B 17/39
[52] U.S. Cl. ................ 606/12; 606/15; 433/215
[58] Field of Search .............. 606/2, 3, 10–17; 433/215; 607/89

[56] References Cited

U.S. PATENT DOCUMENTS

| | | |
|---|---|---|
| 4,648,892 | 3/1987 | Kittrell et al. ............................ 606/12 |
| 4,686,979 | 8/1987 | Gruen et al. .............................. 606/3 |
| 4,784,135 | 11/1988 | Blum et al. ................................ 606/3 |
| 5,020,995 | 6/1991 | Levy ........................................ 433/215 |
| 5,055,048 | 10/1991 | Vassiliadis et al. ..................... 433/215 |
| 5,207,576 | 5/1993 | Vassiliadis et al. ..................... 433/215 |
| 5,401,171 | 3/1995 | Paghdiwala ............................. 433/215 |

*Primary Examiner*—Michael Peffley
*Attorney, Agent, or Firm*—F. Chau & Associates, LLP

[57] ABSTRACT

An improved dental procedure and apparatus where ultraviolet radiation pulses are used to etch selectively both hard tissue and soft tissue in dental procedures. There exists distinct ablation thresholds for hard and soft tissue which are dependent on the material being ablated for a given wavelength of the ultraviolet radiation. Sufficient differences in ablation threshold exist for enamel, dentin, and carious material, thereby allowing dentists to perform both hard tissue and soft tissue procedures without excess damage to healthy enamel, dentin or other pulp structures.

14 Claims, 7 Drawing Sheets

DENTAL PROCEDURES AND APPARATUS USING ULTRAVIOLET RADIATION this is a divisional application of U.S. application Ser. No. 08/506,410 filed on Jul. 24, 1995, now U.S. Pat. No. 5,785,703, which is a divisional application of U.S. application Ser. No. 08/271,385 filed on Jul. 6, 1994, now U.S. Pat. No. 5,435,724, which is a continuing application of U.S. application Ser. No. 08/026,333 filed on Mar. 4, 1993, abandoned.

DESCRIPTION

1. Field of Invention

This invention relates to improved procedures and apparatus for procedures on teeth using ultraviolet radiation, wherein ultraviolet laser pulses having selected energy fluences can be used to perform several different procedures on different materials found in teeth.

2. Background Art

Lasers are optical devices which produce intense and narrow beams of light at particular wavelengths by stimulating the atoms or molecules in a lasing material. Many types of lasing materials are known including gases, liquids and solids. The lasers are typically named in accordance with the element or compound that emits light when energized, such as carbon dioxide, argon, copper vapor, neodymium-doped yttrium-aluminum-garnet (Nd:YAG), erbium, holmium, rare gas halide gas mixtures such as ArF, XeCl, KrF (excimers) etc., alexandrite, ruby, Ti:sapphire and many dyes. When applied to human tissue, the beam of light produced by the laser will be partially absorbed in a process which typically converts the light to heat. This is used to change the state of the tissue for purposes of etching or cutting. In the case of nonultraviolet radiation-producing lasers, the dominant mechanism for cutting or etching is a thermal one. However, in the case of ultraviolet laser pulses having energy fluences in excess of a threshold dependent upon the wavelength of the radiation and the material being irradiated, a "cool" etching is achieved in which there is minimal heat transferred to the surrounding tissues. Instead, the energy of the ultraviolet radiation pulses is primarily transformed into the kinetic energy of the particles which explode or ablate from the tissue being irradiated. This fundamental discovery and its application for both medical and dental purposes is described by S. E. Blum et al in U.S. Pat. No. 4,784,135.

In the development of a laser system for specific dental and medical applications, factors to be considered are the wavelength of the light produced by the laser, the pulse width of the radiation pulses, the energy per pulse, the laser beam spot size on the target and the apparatus and method of delivery of the laser light to the tissue to be irradiated. It is necessary to deliver a precise amount of light to the tissue, whether the mechanism for cutting is a thermal one or ablative photodecomposition as can be achieved through the use of pulsed ultraviolet radiation. If there is application of energy of high intensity to the tissue, rapid absorption and heating can occur which can cause undue damage to areas surrounding the irradiated region. In general, pulse-type operation is preferred rather than continuous wave irradiation, since delivery of a series of pulses provides an additional control over the interaction, absorption of radiation, and the overall process. This leads to more control of the etch depth and the degree of damage to surrounding tissue.

Medical research on the use of lasers has been ongoing for many years. The use of lasers in the field of ophthalmology to correct, for example, myopia, is the subject of considerable research effort where good success is noted. Many different types of lasers have been used, with the more significant results now being produced through the use of rare gas halide excimer lasers providing pulsed ultraviolet radiation. In addition to this application, lasers are now used in a variety of medical applications such as gynecology, urology, dermatology, angioplasty, and plastic surgery. Lasers are also used in general surgery in connection with surgical procedures concerning the ear, nose, and throat as well as in the treatment of gastrointestinal ailments. The generally listed advantages of lasers for some medical applications include reduced surgical pain, reduced infection and bleeding, reduced scarring, and less post-operative pain, as well as a reduced need for post-operative analgesics.

The use of lasers in dentistry has also been the subject of considerable research and development activity. These prior efforts have involved the controlled application of laser thermal effects to soft or hard tissue. Problems to be avoided in such laser dentistry include the destruction of teeth by heat and often unsatisfactory techniques for delivering the laser pulses into confined regions in the mouth. Various types of articulated arms and fiber optic delivery systems have been developed for these latter purposes. At this time, testing of various types of laser systems in laser dentistry is occurring, where the commonly used lasers are the Nd:YAG laser, $CO_2$ lasers, holmium lasers, argon lasers and erbium lasers.

Dentistry involves soft tissue procedures as well as hard tissue procedures. The soft tissue procedures include the removal of excess or diseased gum tissue, contouring of gums, performing biopsies, preparing gums for crown and bridge impressions, trimming the gums to fit the crowns and bridges, treating various types of gum disease and infected pockets between the gum and teeth, and hemostasis (control of bleeding). Hard tissue procedures include drilling, removal of decay from teeth, preparation of teeth for filling, increasing of hardness of dentin to render teeth less susceptible to decay, removing stains, and desensitizing and auesthetizing teeth. U.S. Pat. No. 5,055,048 describes a Nd:YAG dental laser assembly useful for many different dental procedures as outlined therein.

The pulsed Nd:YAG laser has dominated the dental market, but use of this laser is limited to soft tissue treatments, such as removing and shaping gums. This laser provides a wavelength of 1.06 microns which is only slightly absorbed by water. However, the Nd:YAG laser cannot be used effectively to remove hard tissue and is often not as desirable when precise control of heating adjacent tissue is necessary (as for example when a small piece of gum is to be removed without harming an adjacent tooth). A $CO_2$ laser is more appropriate for soft tissue dental applications, but it is not suited for hard tissue use because the energy level needed is very high and causes damage to nearby tissue. In the field of cosmetic and restorative dentistry, an argon laser operating at about 488 nm appears to be preferred. This type of laser can be used to polymerize scalants in pits and fissures and can be used to quickly cure restorative materials.

The erbium laser may be more suitable as a hard tissue dental tool (if used with water) since it may be versatile and safe to use. Another possible candidate for hard tissue applications is a short-pulse, high-energy $CO_2$ laser. However, it is not clear that these types of lasers can be used for all dental applications, it being apparent that their use will be limited to selected dental procedures.

From the foregoing, it is apparent that the development of laser dentistry is in its early stages and that all of the commercially available lasers have inherent disadvantages in terms of their limited applicability to selected dental procedures. A major problem encountered with these lasers is that all of them rely on the absorption of laser energy to produce heat, which in turn is used for tissue removal. This creates problems dependent on the type of material irradiated, as the thermal diffusion and thermal mechanism varies with different materials and is more difficult to control. Because there is heat spreading to regions surrounding the irradiated area, destruction of adjacent tissue is likely to occur. Additionally, the energies used to provide tissue removal are often such that the applications of the laser pulses must be very strictly controlled in area. In many circumstances, it has been found that laser dentistry in its present state does not afford significant advantages over conventionally used instruments such as mechanical drills. Of particular significance is that it is not presently possible to perform drilling operations with most lasers, as none of the commercially available lasers can be used to cut enamel. Still further, none of the commercial lasers works very well to remove dental carries and to provide possibilities for root canal surgery.

In addition to the visible and infrared lasers that have been used for dental procedures, U.S. Pat. No. 4,784,135 describes the use of ultraviolet lasers, such as excimer lasers, for dental work. Generally, pulsed UV lasers are used where the energy fluence per pulse is sufficient to produce ablation. A follow-up article by J. Wynne and R. Lane (Lasers and Applications, p. 59, Nov. 1984) describes ablation of enamel and dentin by UV laser pulses, but does not address removal of carics, critical ablation thresholds or techniques for practical dentistry.

In addition to the foregoing patent, U.S. Pat. No. 5,107,516 describes a two-laser feedback system that employs ablation to remove arterial plaque and mentions possible dental applications. German patent DE 4015 066 A1 describes a technique in which differential reflectometry is used to determine the duration and/or energy of each laser pulse, where the laser can be a UV laser used for removal of dental carics. Another German patent DE 3800555 A1, based on PCT application PCT/DE89/00010, describes the use of an Arl' excimer laser delivery system at 193 μm to ablate hard dental material such as dentin or enamel. A delivery system including a sealed and evacuated articulated arm and reflectors is employed to deliver the UV radiation.

In these prior art systems, UV radiation is used for dental applications but additional means are usually required to ensure safe operation. This is exemplified by DE 4015066 where differential reflectometry is used in a feedback loop to provide laser control so as not to remove healthy tissue. In contrast with this the present invention does not require reflectance or spectroscopic techniques to identify target tissue. Instead, material removal is controlled by utilizing newly discovered differing ablation thresholds for different types of dental material. Based on the discovery and recognition of these different thresholds, various windows of operation are defined which allow a single laser to be used for several different procedures without risk to the patient and without the need for sophisticated target tissue identification.

Accordingly, it is a primary object of this invention to provide improved laser dentistry in which a single laser system can be safely used to do various dental procedures including both hard and soft tissue procedures.

It is another object of this invention to provide improved laser dentistry where the energy fluence per pulse can be changed to allow a laser to do both hard and soft tissue removal.

It is another object of this invention to provide improved laser dentistry which yields minimum cellular destruction to tissue at the margins of the irradiated volume.

It is another object of this invention to provide improved laser dentistry which does not rely on thermal mechanisms as the primary mechanism for hard and soft tissue removal.

It is another object of this invention to provide an improved ultraviolet laser system for dental applications in which the risk of contamination is reduced during the procedure by the use of ultraviolet radiation providing germicidal sterilization.

It is a further object of this invention to provide laser pulse removal of hard tissue in a safe and effective manner.

It is another object of this invention to provide an ultraviolet dental procedure and apparatus in which ablative photodecomposition is used to provide windows of operation wherein the same laser can be used for both hard and soft tissue applications and wherein automatic control of the laser output pulses is obtained.

It is another object of this invention to provide an improved laser technique for fluoride treatment of teeth.

BRIEF SUMMARY OF THE INVENTION

A technique and apparatus for improved laser dentistry are described in which pulsed ultraviolet light, preferably from a laser, is used to selectively remove tooth material. By directing the laser beam onto the surface of the tooth at a location where material is to be removed, carious lesions, dentin, and enamel can be removed to a controllable depth by using the correct combination of laser fluence and number of pulses, with minimum damage and heat being produced in the tooth at the margins of the excised material. Ultraviolet light, at an energy fluence above the threshold for removing tooth material, is absorbed in a thin layer of irradiated material and is delivered in a time that is short compared to the time for the absorbed energy to thermally diffuse into adjacent volumes. In the practice of this invention, pulsed ultraviolet light can be used to ablate carious material, dentin, or enamel, each with a defined energy fluence threshold below which the material is not removed. This provides windows of operation, or energy regions of tolerance, enabling a dentist to safely use an ultraviolet laser in several procedures. The depth of material removed per pulse increases for increasing fluence above the threshold. Unexpectedly, the threshold for removal of carious material by UV light was greater than that for dentin. However, for a given fluence above threshold, the amount of carious material removed is much greater than the amount of dentin that is removed.

An apparatus suitable for the delivery of laser radiation having selectable energy fluence can be provided by an optical system using a series of mirrors and lenses to focus the laser beam onto the tooth to be irradiated. As an alternative, the laser energy can be delivered by an optical fiber delivery system having suitable optics (lenses, etc.) at the end of the fiber to direct the laser beam into the fiber and to focus the light emerging from the fiber onto the tooth. A beam homogenizer may be used to ensure that the beam is uniform in intensity to avoid the presence of hot spots. This can be done by a series of lenses or by a series of highly transmitting channels that cause the various parts of the beam to crisscross and overlap. If an optical fiber is used, total internal reflections will accomplish this result. Means are provided to allow the dentist to manipulate the tool to direct the laser beam to the desired place on the tooth.

The pulsed ultraviolet radiation can be provided by any source that produces radiation having energy fluences sufficient to meet the threshold for removal of the particular material of the tooth to be irradiated. Excimer lasers are available for providing various ultraviolet wavelengths, for example at 193 nm, 248 nm, 308 nm, and 351 nm. Solid state lasers such as frequency-multiplied near infra-red or visible lasers such as Nd:YAG and Ti:sapphire, diode lasers and microlaser or microlaser arrays can also be used. U.S. Pat. No. 5,144,630 describes several solid state lasers which can produce coherent radiation at multiple wavelengths in the ultraviolet range and infrared range. Since DNA has an absorption peak at about 250 nm, it may be preferable to avoid lasers providing an ultraviolet output near this wavelength. Particularly suitable wavelength ranges appear to be about 185–220 nm and 300–400 nm.

Automatic feedback control systems based on the unique ablation characteristics of the specific material (enamel, dentin and carries) being ablated are described. These systems can also be used to alert the dentist about the presence of harmful biological contaminants, and to control the UV laser pulse repetition rate to ensure patient comfort.

These and other objects, features, and advantages will be apparent from the following more particular description of the preferred embodiments.

DETAILED DESCRIPTION OF THE PREFERRED EMBODIMENTS

When human teeth are exposed to pulsed ultraviolet light from a laser above a threshold energy fluence, material will be ablated from the surface of the tooth.

Below the threshold energy fluence, no material is removed. It has been discovered that healthy enamel, healthy dentin, and carious lesions each have different energy fluence thresholds for ablation, as well as different absorption coefficients which describe the characteristic depths to which UV radiation is absorbed in the different materials. This allows the use of a single UV laser system to accomplish several dental procedures safely, in which different windows of operation can be defined.

Figure 1:
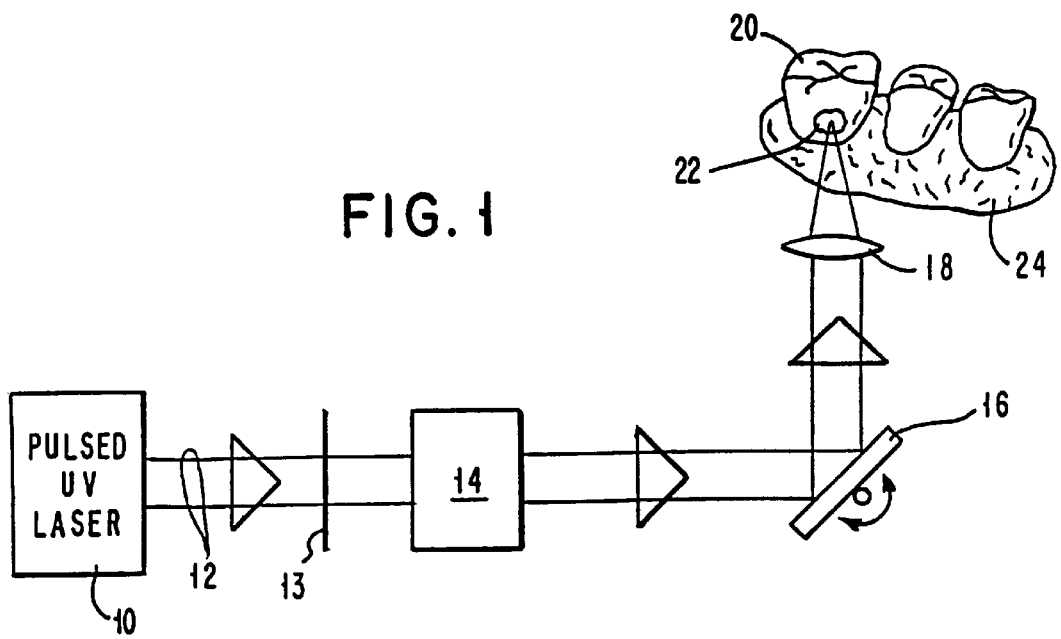
FIG. 1 is a schematic illustration of an apparatus for applying suitable pulsed ultraviolet radiation on a tooth, using a series of reflectors and lenses together with a beam homogenizer to provide pulsed laser radiation of proper wavelength and energy fluence.
Figure 2:
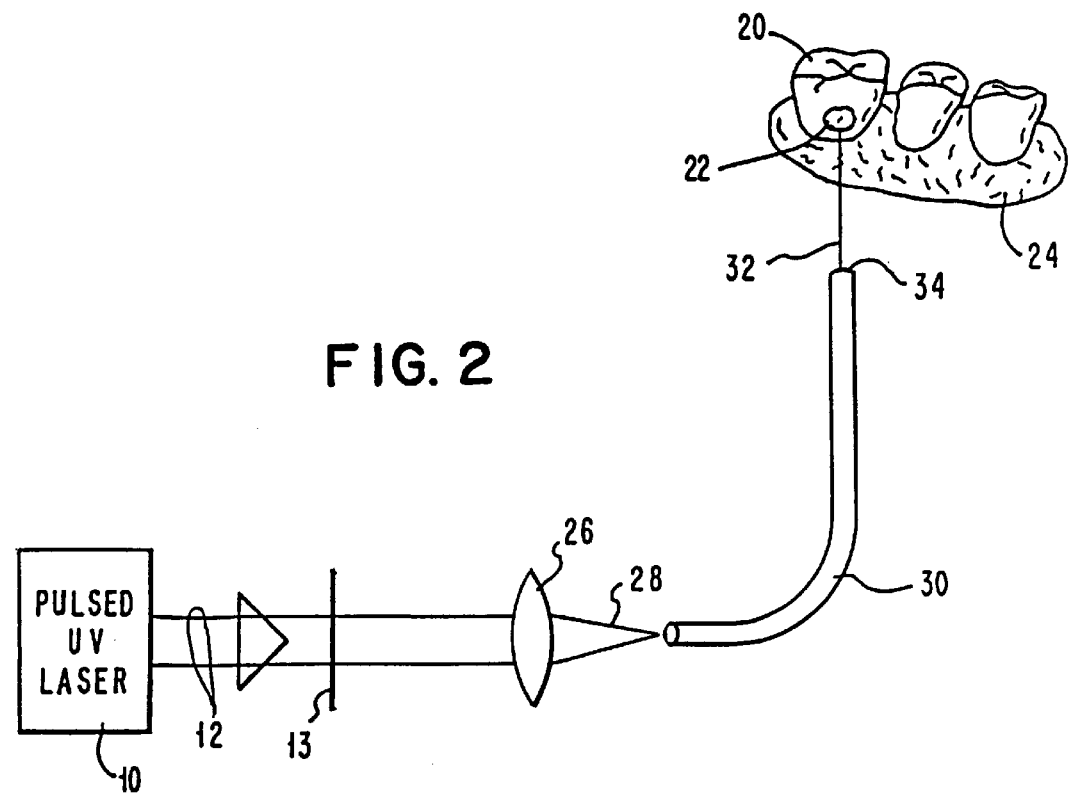
FIG. 2 is a schematic illustration of another apparatus for performing laser dentistry in accordance with the present invention, where an optical fiber delivery system is utilized.

FIGS. 1 and 2 illustrate suitable forms of an apparatus that can be used to deliver ultraviolet radiation to teeth.

In FIG. 1, a pulsed ultraviolet laser 10 provides a light beam 12 in the wavelength range less than about 400 nm. Rare gas halide excimer lasers can be used as the radiation source for providing ultraviolet outputs at 193 nm (ArF), 248 nm (KrF), 308 nm (XcCl), and 351 nm (XcF). Additionally, a solid state laser such as a frequency-tripled Nd:YAG can be used to provide an output at 355 nm. In order to be able to block the laser beam 12 on demand, a shutter 13 is provided. A beam homogenizer 14 is optionally provided to ensure that the beam is uniform in intensity. Beam homogenizers are known in the art, as can be seen by referring to Y. Ozaki and K. Takamoto, *Applied Optics*, Vol. 28, p. 106 (1989). In a particular embodiment, homogenizer 14 can be comprised of a series of lenses (Y. Ozaki et al., ibid) or a series of highly transmitting channels (M. Wagner et al., *Measurement Science and Technology*, Vol. 1, p. 1193 (1990)) that cause the various parts of the beam to crisscross and overlap, thereby smoothing out intensity variations and eliminating hot spots. Since excimer lasers are multi mode lasers, hot spots may occur. The homogenizer generally breaks the beam into small beamlets which are then recombined to provide a more uniform intensity across the beam cross section.

Beam 12 is then directed to a rotatable mirror 16 from which it is reflected to a lens 18. The lens is chosen to have a focal length sufficient to cause a focused point of light to be delivered to the tooth 20, and particularly to a localized area 22 to be irradiated. Area 22 can be, for example, an area of a lesion, such as a carious lesion on the tooth. In FIG. 1, the teeth are schematically illustrated as is a section of the person's gum 24. In practice, the apparatus (even including the laser 10) can be located in an articulated arm of the type commonly used by dentists.

As an alternative, the rotatable mirror 16 and lens 18 can be replaced by a curved concave mirror. This will deflect the light beam and also focus it. A mirror with a coating of a highly reflective material, such as Al or a multilayer dielectric, can be used.

FIG. 2 shows another embodiment for an ultraviolet delivery system to a tooth to be irradiated. Components having the same function as those shown in FIG. 1 are given the same reference numeral. Thus, the laser 10 in FIG. 2 provides output laser pulses 12 of wavelength less than about 400 nm. Shutter 13 is used to block the light beam 12 as desired by the dentist. A lens 26 is used to direct and couple the focused laser beam 28 into an optical fiber 30, which carries the laser pulse. The laser pulses exit fiber 30 to provide a pulse train 32 which impinges upon tooth 20, and particularly on the area 22. Due to the multiple total internal reflections which occur in fiber 30, beam homogenization will automatically occur to ensure that the output beam 32 is sufficiently uniform in intensity over its cross section.

The apparatus of FIG. 2 is desirable since the dentist can hold in his/her hand a tool consisting of the delivery end of the optical fiber delivery system. The dentist can then manipulate this tool to direct the laser beam to the desired place (22) on the tooth. A very short focal length lens 34 located at the delivery end of optical fiber 30 enables the dentist to hold the tool close to the tooth and to provide a very focused beam at the area 22 to be irradiated. The end of the fiber can be shaped to provide a lens, or a lens can be attached to the delivery end of the fiber. Thus, material will be ablated from the tooth in a very controlled area easily observed by the dentist.

EXAMPLES

Quantitative experiments were performed on human dentin, enamel and carious lesions. Approximately 2 mm thick cross sections were cut from the middle third of the crowns of several molar teeth using a Buchler Isomet saw with a diamong wafering blade. Both surfaces of each section were polished with 320 followed by 600 grit wet carbimet polishing paper. Sections were then immersed in 6% citric acid and shaken for 2 minutes to remove the smear layer. They were then rinsed with deionized water and stored in 70% ethanol. Carefully selected areas of these cross-sectioned human teeth were exposed to a given number of pulses of light from a 308 nm XcCl excimer laser at a given fluence. Using a mechanical profilometer, the depths of the resulting ablation trenches were measured. The beam energy fluences were then plotted on semi-log paper as a function of ablation trench depth per pulse, and a straight line was fitted to the data. Assuming Beer's law correctly described the absorption of the UV radiation within the tooth, the following expression will describe the relationship between the amount of material removed and the applied energy fluence:

$$F = F_o e^{-\alpha l},$$

where F is the fluence of the laser beam at a depth l into the irradiated tooth, $F_o$ is the fluence of the UV radiation at the surface of the region being irradiated, and $\alpha$ is the absorption coefficient for the dental material being ablated.

By measuring the depth d per pulse of an ablated hole as a function of laser fluence, the fluence threshold for ablation $F_{th}$ and the coefficient $\alpha$ for the ablated material can be determined:

$$F_{th} = F_o e^{-\alpha d}$$

The energy per unit volume l: being deposited at a depth l in the irradiated material is the product of the energy fluence F at that depth and the slope $\alpha$ of the logarithm of the applied fluence versus depth plot. Thus $$E = l'\alpha$$

When the energy per unit volume E exceeds the threshold energy per unit volume $E_{th}$, ablation will result. Since the slope $\alpha$ is a constant for each dental material (enamel, dentin and carious material), $$E_{t/t} = F_{t/t} x$$

Figure 3:
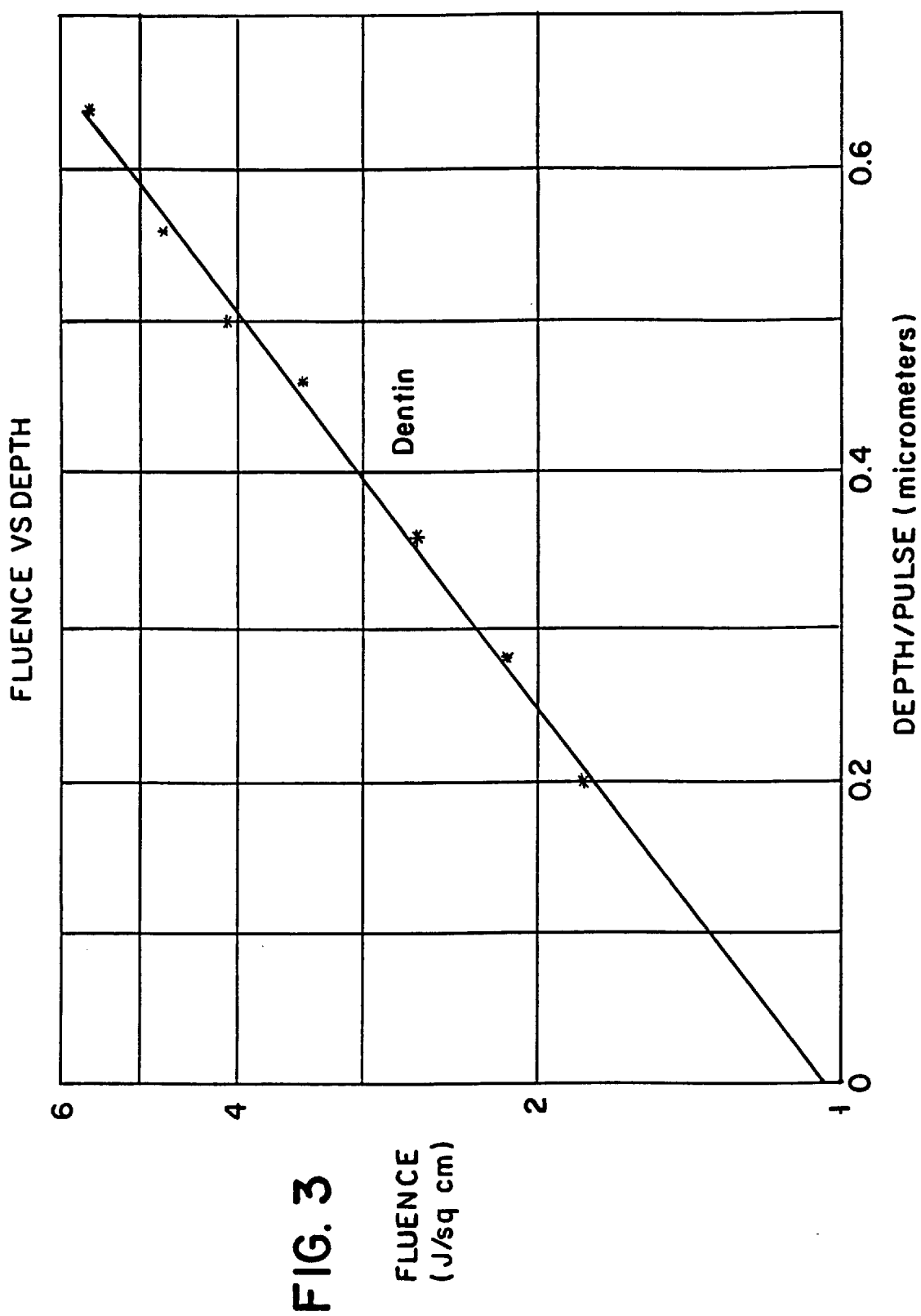
FIG. 3 is a plot of energy fluence versus etch depth per pulse for the ablative photodecomposition of dentin, using pulsed ultraviolet radiation at 308 nm.
Figure 4:
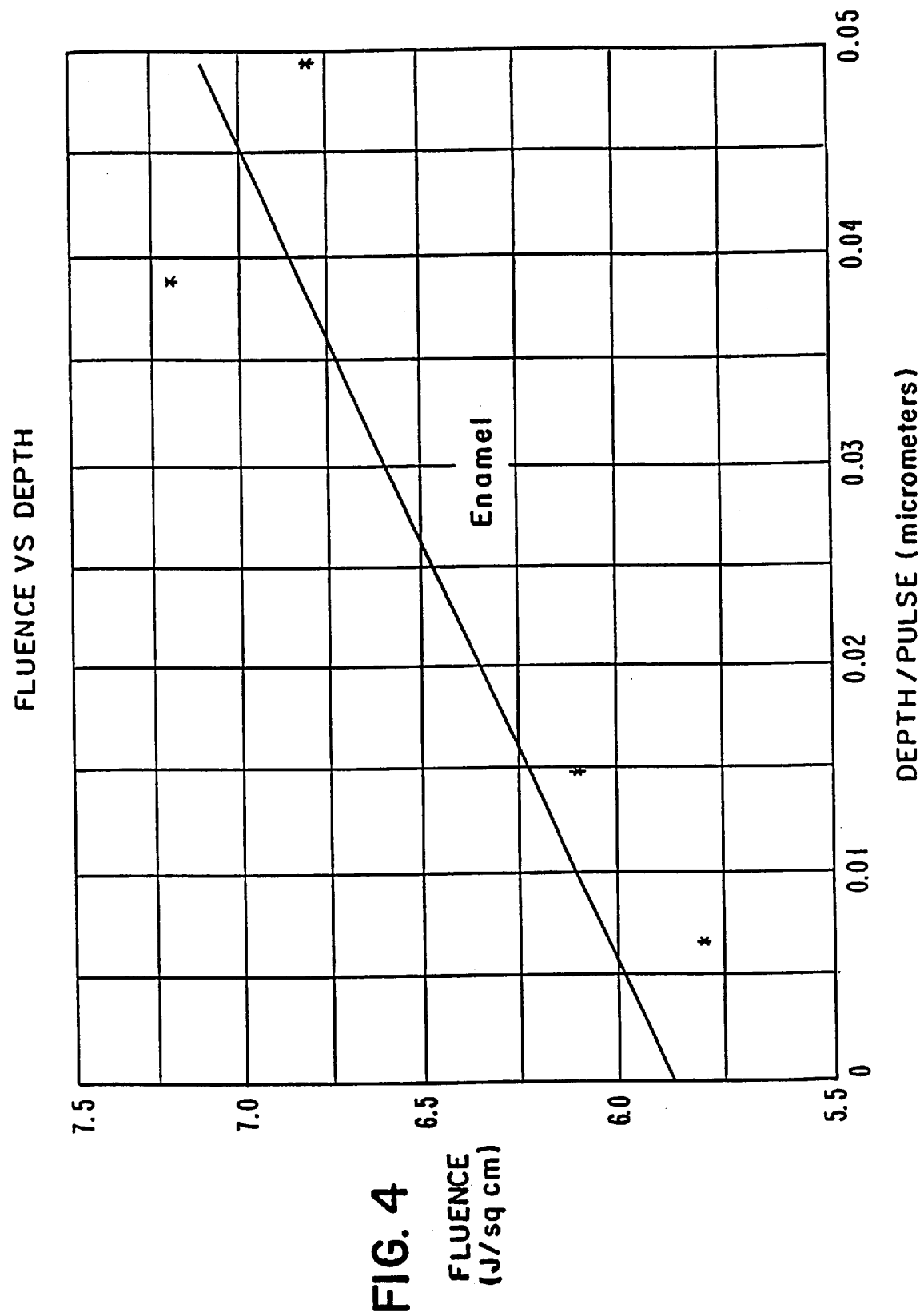
FIG. 4 is a plot of energy fluence versus etch depth per pulse for the ablative photodecomposition of enamel, using an excimer laser providing an output radiation at 308 nm.
Figure 5:
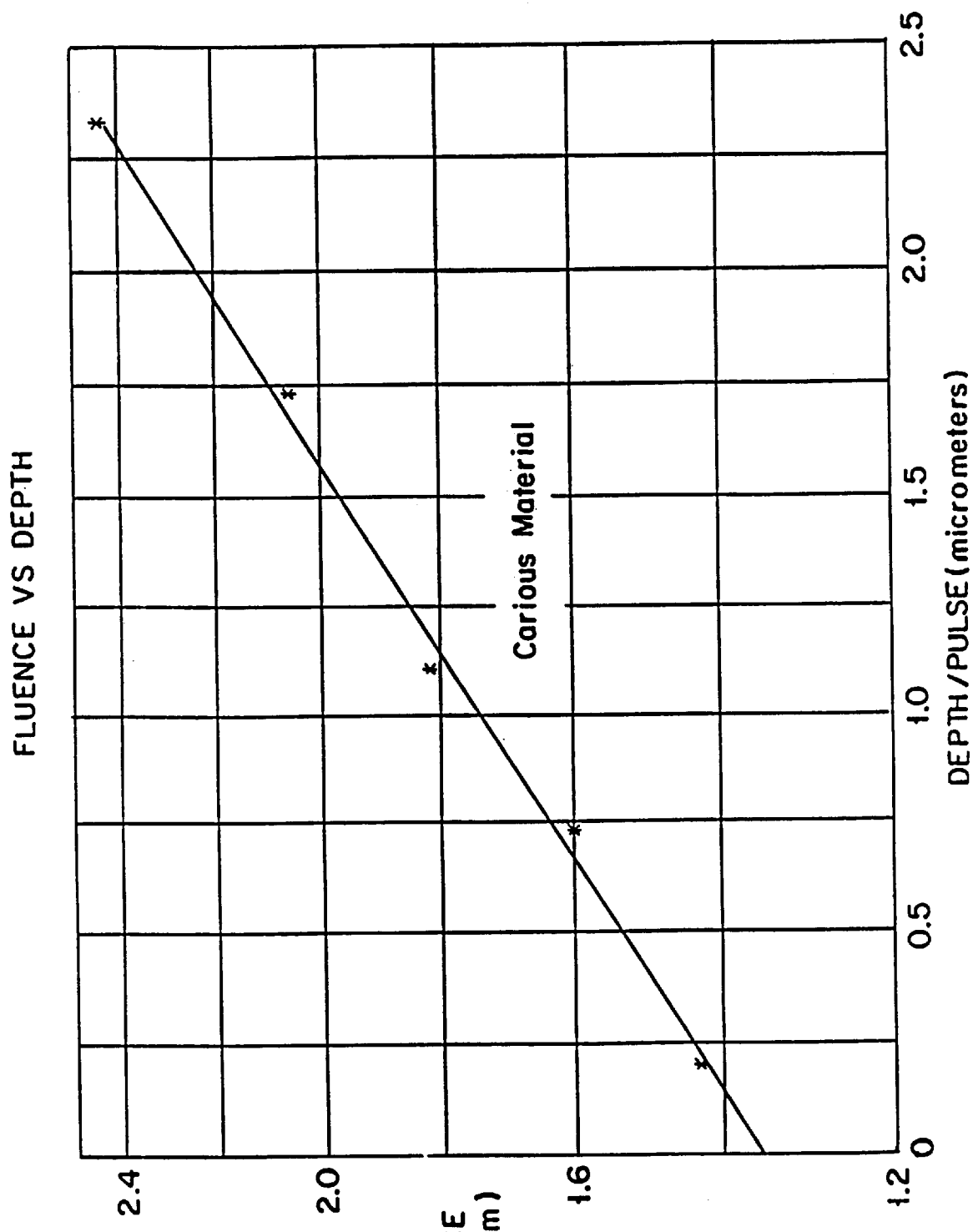
FIG. 5 is a plot of energy fluence versus etch depth per pulse for the removal of carious material using ultraviolet light pulses at 308 nm.
Figure 6:
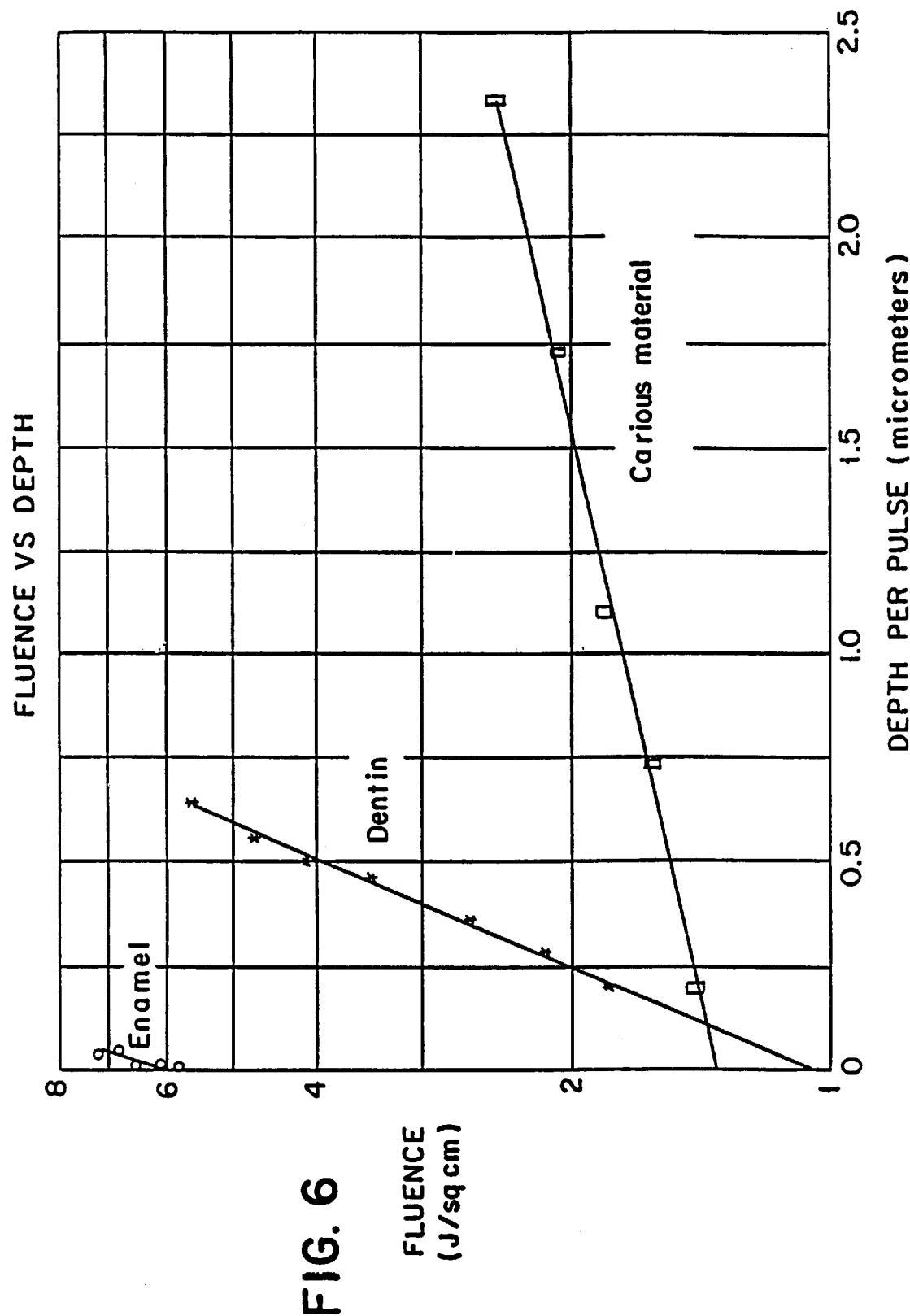
FIG. 6 is a combined plot of energy fluence versus etch depth per pulse for the removal of enamel, dentin and carious material using ultraviolet radiation pulses at 308 nm. The data from FIGS. 3–5 are plotted on a common scale to facilitate comparison of ablative photodecomposition of enamel, dentin and carious material.

Plots of data for the ablation of dental materials are shown in FIGS. 3–6. FIG. 3 illustrates the data for dentin ablation, FIG. 4 illustrates the data for enamel ablation, and FIG. 5 illustrates the data for ablation of carious material. FIG. 6 is a plot which combines the data in FIGS. 3–5.

Referring to FIG. 3, for dentin, the ablation threshold fluence, $F_{th}$, is 1.04±0.06 J/cm$^2$ and the absorption coefficient $\alpha$ is 2.7±0.1 $\mu$m$^{-1}$. The energy threshold $E_{th}$ is thus 2.8×10$^4$ J/cm$^3$.

Referring to FIG. 4, for enamel $F_{th}$ is 5.9±0.3 l/cm$^2$, $\alpha$ is 3.8±1.5 $\mu$m$^{-1}$, and $E_{th}$ is 22×10$^4$ J/cm$^3$.

The ablation depth per pulse for dentin is approximately 0.3 $\mu$m for an incident fluence of 2.3 J/cm$^2$, at which fluence enamel would not be ablated. For enamel, the ablated depth per pulse is approximately 0.03 $\mu$m for an incident fluence of 6.6 J/cm$^2$. From these measurements, it is apparent that there is a wide window of fluence where dentin can be ablated without removing or damaging enamel that is unavoidably exposed to the laser beam.

Experiments were also performed to determine the threshold energy fluence for the ablation of carious material. These studies were performed at 308 nm using an excimer laser. A tooth having caries therein was preserved with an alcohol solution and then a flat surface was made by polishing with emery paper. This facilitated visual inspection before and after irradiation to determine the etching effect of the ultra-violet laser pulses. Five holes of about 0.3 mm$^2$ cross-sectional area were then etched into the carious material by application of UV laser pulses of different fluence. The depth per hole was measured using a mechanical profilometer profilometer, and the resulting data are plotted in FIG. 5. As noted in FIG. 5, $F_{th}$ for carious material was determined to be 1.36 J/cm$^2$, while the slope ($\alpha$) of the curve is 0.25 $\mu$m$^{-1}$. $E_{th}$ for carious material is thus 0.34×10$^4$ J/cm$^3$.

The foregoing experiment was then repeated with the same tooth, after rinsing with an alcohol solution and polishing a different region of the tooth. Five new holes were etched into the carious material. The same mask was used as was used in the first experiment, the holes being about 0.3 mm$^2$. in cross-sectional area. Again, the depth of each hole was measured and plotted against the known energy fluences that were applied. The wavelength of the incident radiation is again 308 nm. The results were essentially identical to those of FIG. 5.

It was initially surprising that the energy threshold for ablation of dentin is less than that for carious material. Since carious material is primarily organic in nature, it was expected that the ablation threshold for the carious material would be less than that for the harder dentin material. However, as noted above, it is the threshold energy per unit volume which must be exceeded in order to have ablation. Comparing the slope of the curve in FIG. 5 with that in FIG. 3 indicates that the curve in FIG. 5 is much flatter than the curve in FIG. 3 for dentin ablation. Thus, the absorption coefficient $\alpha$ for carious material is less than that for dentin, the energy threshold is more than 8 times smaller and much more carious material will be removed than healthy dentin for the same fluence of applied ultraviolet energy. The amount of carious material removed at a given energy fluence can be as high as ten times that of the amount of dentin removed. Since the light penetrates deeper into carious material, a higher threshold fluence is required to produce ablation for caries, in contrast with the ablation threshold for dentin, where the light penetrates less. When operating above the threshold energy for carious material, dentin will be ablated as well as carious material, but the amount of dentin that is ablated will be significantly less than that of the carious material. The data for FIGS. 3–5 are plotted in FIG. 6 on a common scale, to facilitate comparison. FIG. 6 illustrates the different thresholds and rates of removal of these different types of tooth material.

In order to provide a safety factor, i.e., not to excessively ablate healthy dentin when it is desired to remove carious material, a "signature" is required to indicate to the dentist the nature of the material being ablated. Above the threshold fluence for caries, a loud popping sound will be heard, accompanied by an orange-colored plume. When all of the carious material has been removed and healthy dentin is exposed to the ultraviolet pulses, the popping sound will become softer because the amount of material being ablated is less. This provides an indication of the material being ablated.

One way to view the ablation process is that sufficient energy per unit volume must be deposited in the material to turn it into a gas. The material will expand and blow out of the etched hole. The energy fluence must be sufficient high that the energy per unit volume will cause this to occur. Whether the mechanism is characterized as thermal bond breaking or photochemical bond breaking is not germane to the successful removal of all types of dental tissue in accordance with this invention. The term ablative photodecomposition, or ablation, is used in a generic sense to include both thermal bond breaking and photochemical bond breaking where the application of ultraviolet radiation occurs in a manner to blow away irradiated material at a rate sufficient that there is minimal thermal diffusion into the nonirradiated material. It is recognized that, if the repetition rate of ultraviolet pulses is too high or if the pulse width is too great, the ablation products will not be able to "blow-off" from the irradiated material fast enough to prevent excess thermal diffusion. In this case, thermal damage of the edges of the irradiated region could result.

A signature of ablation is an easily discernible popping sound that is synchronous with the laser pulses. This sound is heard only when material is ablated, as confirmed by post-ablation measurements. The sound is generated by gaseous material ablating off the surface. Accompanying this sound is an orange-colored "jet" emanating from the ablated surface. These two signatures become more pronounced with increasing fluence above threshold. They are absent below the ablation threshold. Consequently, this sound and the orange-colored jet present a simple and immediate way to determine what sort of material is being ablated by the laser pulses. For a given fluence above the threshold for ablating enamel, the popping sound and jet size are much more pronounced when this fluence is directed onto dentin than onto enamel. Therefore, when ablating enamel at the surface of a tooth, the popping sound and orange-colored jet will strengthen dramatically as soon as the ablation trench has penetrated through the enamel to the underlying dentin. This provides an in-situ indicator to reduce or shut off the laser fluence to prevent unwanted penetration into the dentin. Of course, the dentist can also stop to observe the results of the UV irradiation at any time during the procedure.

Decayed material, which is predominantly organic, has an ablation threshold below that of enamel. Decayed material was selectively removed from underlying dentin and enamel using an energy fluence of 2.3 J/cm$^3$ (308 nm), well below the threshold fluence for ablating enamel. Additionally, an energy fluence of 2.3 J/cm$^2$ was able to ablate decayed material more effectively (i.e., at a significantly greater rate) than dentin, as indicated by the more pronounced popping sound and orange jet signatures.

It has been found that organic materials in dentin tubules can be removed by UV laser radiation at thresholds less than the ablation threshold for dentin. The organic material in the tubule is removed without the necessity for clogging the tubules. This selective ablation technique may therefore assist in desensitizing teeth.

As noted, other UV wavelengths can be used. The selection of 308 nm for the experiments illustrated in FIGS. 3, 4, and 5 was based on the existence of optical fiber delivery systems for 308 nm radiation, these optical fibers being capable of transmitting sufficient energy fluence for material ablation. Examples of materials suitable for optical fibers at this wavelength are the following: quartz, fused silica, and selected sapphires.

Lens material suitable for application with ultraviolet wavelengths include those fabricated of quartz, calcium fluoride, magnesium fluoride, fused silica, and UV sapphire.

This laser system has also been shown to remove stain from teeth. In almost all cases, staining is a discoloration of the organic pellicle overlying the enamel. This material is organic in nature and consists of salivary proteins which form a deposit of only a few microns thickness. Instead of removing stain in the traditional way using an abrasive technique, ultraviolet pulses can be used. The organic stained material has an ablation threshold below that of normal enamel and can be easily removed without affecting the underlying enamel. Tartar, or calcified plaque, can also be removed by UV radiation.

It may also be possible to use ultraviolet laser radiation to provide dentin desensitization for those people who have very sensitive teeth. This desensitization would be achieved by creating a sufficient increase in temperature to cause the dentin tubules to be sealed.

As reported by B. D. Goodman and H. W. Kaufman in the J. Dental Research, page 1201, October 1977, laser radiation can be used to enhance fluoride uptake into human tooth enamel and also reduces enamel dissolution in acid and therefore its susceptibility to tooth decay. In this prior work, an argon laser was used at a wavelength of 514.5 nm. In a later work, a $CO_2$ laser was shown to be even more effective (J. of the Japanese Society of Laser Medicine, vol. 6, pp. 231–234, 1986). In the practice of the present invention, an ultraviolet laser source can be used in combination with a fluoride carrier in which the fluoride (NaF or another fluoride) is dissolved in a solution that does not char upon laser light exposure. The fluoride carrier can range from water to compounds that will dissolve fluoride but not char upon irradiation. The fluoride carrier is preferably an inorganic carrier which will not char under UV irradiation, where the carrier is at least about 70% transparent to UV radiation. This radiation is applied at an energy fluence less than that which will cause ablation of the tooth material. Further, the total thickness of the fluoride containing layer is less than that which would make the transmission of the UV radiation to the tooth surface less than about 70%. A suitable thickness is typically less than about 1–2 mm. Fluorapatite production on the tooth surface will be enhanced without total energy absorption sufficient to increase the tooth temperature to an amount which would cause pain or damage.

It is also possible to provide both ultraviolet lasers and lasers which produce infrared radiation or visible radiation for operation on soft tissue. As an alternative, a single laser which is capable of generating both infrared and ultraviolet light can be used. Such a laser may be, for example, a frequency multiplied solid state infrared laser such as Nd, Ho, or Hr:YAG, or a Ti:sapphire laser, or diode lasers. Since it is difficult to provide lenses which transmit well in both the UV and IR wavelength ranges, the alternative structure, i.e., the use of a curved concave mirror in place of the plane mirror 16 and lens 18 in FIG. 1, is preferred when combined UV and IR wavelengths are used. Interspersed pulses of IR radiation can also be used for sterilization purposes.

In order to prevent the excess build-up of water that is used for cooling during drilling, it is common to remove by suction carious material as well as blood, tissue, saliva, and water spray. Since the dentist's drill may be subject to contamination, the drill has to be regularly sterilized. In contrast with this, the application of laser pulses is a non-contact technique in which the ultraviolet radiation itself can be used to sterilize the mouth during dental treatment. The UV light is reduced in intensity below the ablation threshold for this purpose. This type of ultraviolet treatment can be undertaken before or after the ablation procedure or, as an alternative, lower power UV pulses can be interspersed among the ablation pulses to neutralize the plume that develops during ablation.

An easy way to do this is to use a beam splitter to split the ablation pulses into two pulses where one of the pulses is delayed. If desired, the delayed pulse can also be reduced in intensity. The delayed pulse is used to minimize or remove the bioactivity of the plume.

Figure 7:
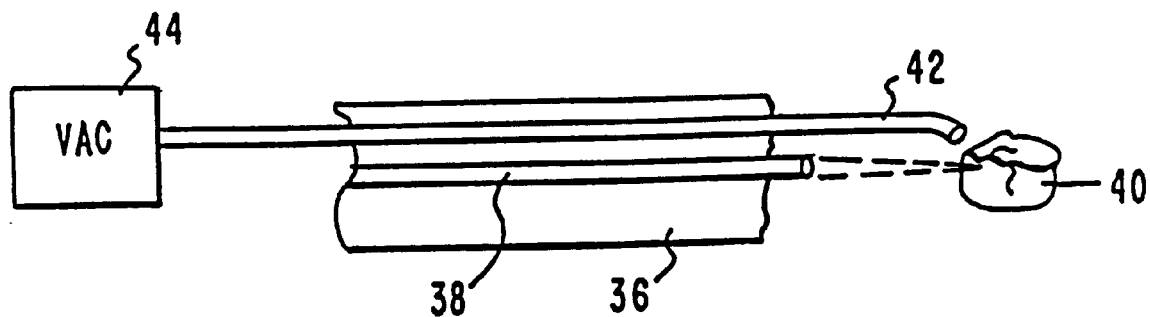
FIGS. 7 and 8 schematically illustrate a dental tool in accordance with the present invention where a suction tube is used to remove particulates and other matter in the plume of ablated material from a tooth.

The plume consisting of particulates blown off from the ablation site, including any other matter, can be evacuated by suction during the ultraviolet ablation process. FIG. 7 shows one possible technique for doing this in which a tool 36 held by the dentist contains both an optical fiber 38 for delivering the ultraviolet radiation to the tooth 40, as well as a small tube 42 which acts as the inlet end for a suction mechanism connected to the vacuum pump 44, and then to a filter (not shown).

Figure 8:
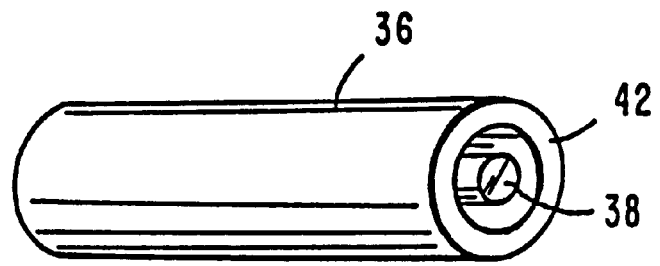

As an alternative, the suction tube 42 can be an anular tube that is coaxial with the optical fiber 38, as shown in FIG. 8. Both the fiber 38 and the anular suction tube 42 are located in the dental tool 36.

The pulse width and pulse repetition rate of the ultraviolet laser pulses are chosen so that the dominant mechanism for removal of material is ablative photodecomposition in which there is minimal heat diffusion to surrounding areas of the teeth or gums. While the ablation threshold must be met or exceeded in order to have ablative photodecomposition, the upper limit on the energy fluence of the pulses is that which would cause excessive heat or damage, i.e., energy beyond that which is desired for etching. Further, the pulse repetition rate and the width of the optical pulses are also chosen with these parameters in mind. Excimer lasers are presently available which provide repetition rates of about 1–2000 Hz where the typical pulse duration is about 10 nanoseconds. Pulse broadening to about 50–100 ns can be used to minimize fiber damage. Excess thermal diffusion (which can cause pain and/or charring) is prevented if the pulse width is less than about 100 ns for repetition rates less than about 20 Hz. For larger pulse widths and/or higher repetition rates, water cooling can be used to reduce undesirable thermal effects.

In addition to the excimer lasers previously described, nitrogen lasers are available which provide ultraviolet light at 337 nm; however, these lasers are usually of very lower power. Also, fluorine lasers are available providing outputs at 157 nm. Various commercial lasers operating at 193 nm are available having pulse repetition rates of 200 pulses per second where the pulse width is about 15 nanoseconds. Corrective lens elements can be used to provide rounded-square spot sized of 0.5 mm by 0.5 mm, or less.

Figure 9:
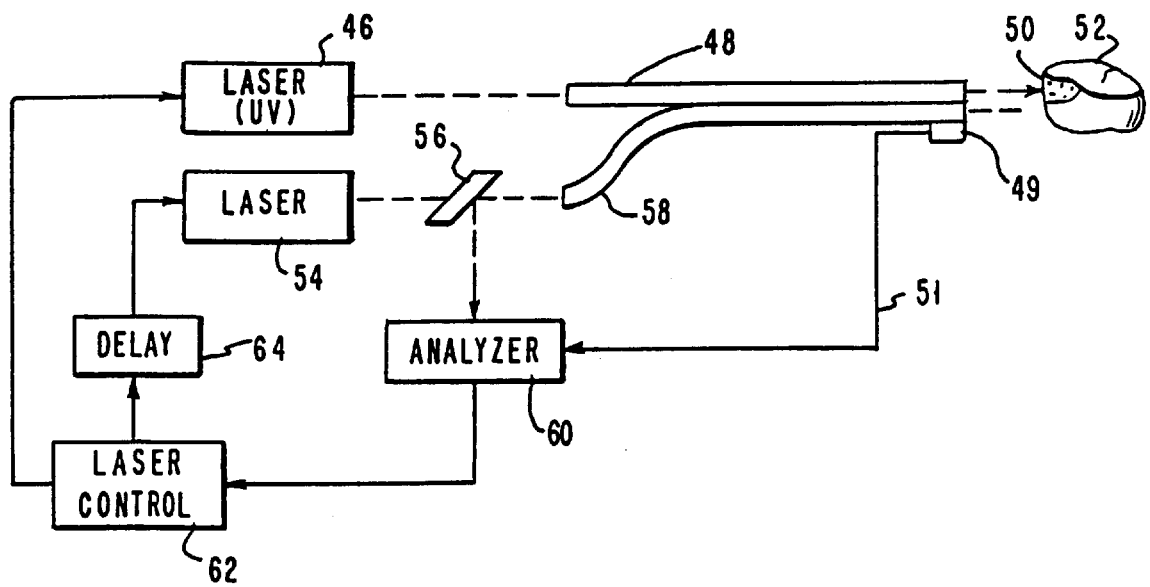
FIG. 9 is a schematic illustration of a laser dental tool which uses the signature of the type of tooth material being ablated to automatically adjust the characteristics of the UV laser ablation pulses.

FIG. 9 schematically illustrates a laser dental apparatus which uses a "signature" of the ablated material (enamel, dentin, or carious material) in order to automatically adjust the power output of the laser which produces the UV pulses for ablation of the tooth material. In this manner, the dentist does not have to rely only on his/her expertise in determining the type of material which is ablated. This can provide a very sensitive control of the energy fluence/pulse, pulse repetition rate, etc. of the laser output so as to minimize the removal of material that is not to be ablated.

In more detail, a laser 46 (excimer, frequency multiplied solid state laser, etc.) provides ultraviolet pulses which are coupled into a delivery system such as an optical fiber 48 for delivery to an area 50 of the tooth 52. These UV laser pulses will have an energy fluence/pulse sufficient to provide ablation of the tooth material being irradiated, where the material can be either enamel, dentin, or carious material. As noted previously, ablation of these different materials occurs at different energy thresholds, and the ablation produces different signatures. Both the "popping sound" and the orange-colored jet emanating from the ablated surface are different when the surface being ablated is enamel, dentin, or carious material. For example, the orange-colored jet will strengthen and/or change color when dentin is ablated, in contrast to when enamel is ablated (at the same energy fluence). When decayed material is being ablated, the ablation will occur at a significantly greater rate than the ablation of dentin, which in turn will provide a more pronounced popping sound and a more pronounced orange-colored jet. A sensor which detects either or both this popping sound and the orange-colored jet is used to provide a control signal to the laser 46 to control the properties of its output pulses.

In FIG. 9, a second laser 54 provides output radiation pulses which pass through dichroic mirror 56 and enter optical fiber 58 for delivery to the region of the plume emanating from the ablated area 50. Depending upon the material being ablated, different strengths of the orange color will appear, providing different wavelengths and/or intensities back into fiber 58. This return signal reflects from mirror 56 to a detector/analyzer 60. Depending upon the color signature of the plume, a signal is provided to the laser output control unit 62. Control unit 62 provides a signal to laser 46 in order to adjust its output power, repetition rate, etc. in accordance with the type of material to be ablated.

The output pulses from laser 54 can be delayed with respect to the pulses from laser 46, by using a delay unit 64 between the control unit 62 and the laser 54. In this manner, the output from ablation laser 46 can be quickly adjusted as soon as the detector/analyzer 60 notices that a different material is being ablated from region 50 of the tooth 52. Delay unit 64 can be omitted if the system is designed to use the first few ablation pulses for analyzis of the material being ablated. After analysis, the control unit 62 would adjust laser 46 to set the proper energy of the UV laser pulses.

To provide control using the signature popping sound, a small acoustic sensor 49, or fiber optic pressure sensor or fiber optic microphone is located at the end of fiber 58, to allow it to be close to tooth 52. Sensor 49 is a transducer which provides an electrical signal that is sent to the analyzer 60 along line 51. The rest of the feedback control is the same as that described hereinabove.

Figure 10:
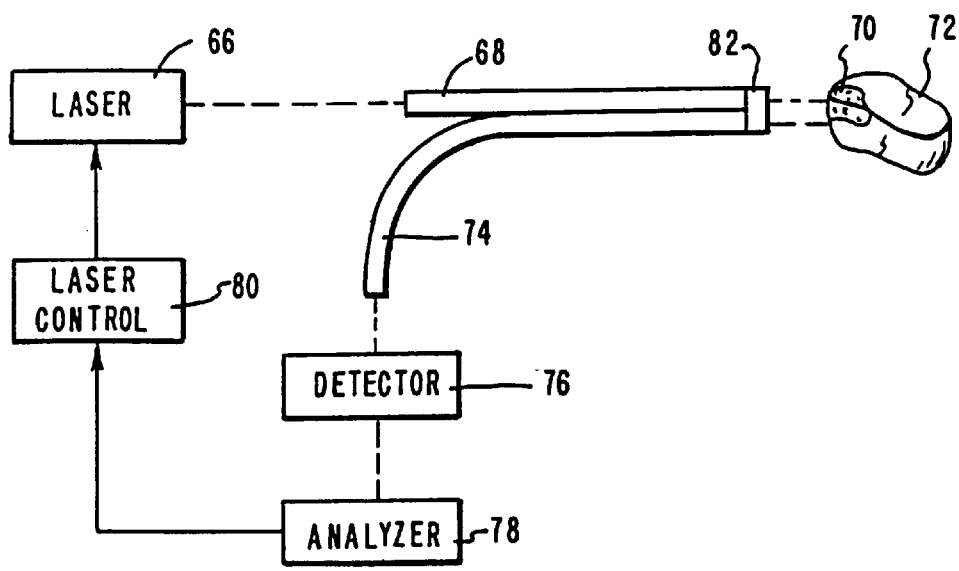
FIG. 10 is a schematic illustration of a laser dental tool which can be used to protect the dentist from contamination by adverse biological products produced in a patient's mouth during UV laser treatment.

FIG. 10 schematically illustrates a laser dental apparatus which can be used to protect against the occurrence of biological contamination, such as hepatitis, IIIV, etc. In this apparatus, a fiber optic biosensor is used to provide recognition of biological conditions in the patient's mouth. For example, if the fiber optic sensor detects the presence of a selected virus in the material being ablated from the tooth, a feedback signal can automatically stop the ablation laser, or trigger the ablation laser to operate at a lower power in order to provide a germicidal effect in which the unwanted virus is destroyed or minimized, while not causing further ablation of the tooth (and therefore stopping the production of additional airborne biological contaminants). This contrasts with the problem of aspirating contaminated material from patients when conventional mechanical drills are used.

In FIG. 10, a laser 66 provides UV output pulses that are coupled into optical fiber 68 for delivery to a region 70 of the tooth 72 to be irradiated. Another optical fiber 74 transmits a response from the area of the irradiated section 70 to a detector 76. The output of the detector is sent to an analyzer 78 which determines what, if any, harmful biological material is present in the plume emanating from the irradiated region 70 when it is ablated. The analyzer 78 then provides a signal to the laser control unit 80, which in turn provides a signal to laser 66 in order to either turn off laser 66, or to reduce the energy/pulse of the UV pulses from this laser, or in some other way to alert the operator (for example, an alarm or indicator light).

A layer 82 of a biologically sensitive recognition element (such as an antibody, DNA or a chemical) is located at the distal ends of fibers 68 and 74. Dependent on the signal received from the area of the irradiated region 70, layer 82 provides a biosensor function, i.e., it recognizes biological material in the vicinity of the irradiated region. This material causes a change in the light reflected to the detector along fiber 74. Different types of fiber optic sensors, including biological recognition elements, are described in an article by David R. Walt, appearing in the Proceedings of the IEEE, Volume 60, No. 6, June 1992, at page 903. The indicating layer 82 modulates light sent down the fiber from the laser 66. The amount of modulation of the return light from the area surrounding the irradiated region 70 can be a measure of the amount (including presence/absence) of a particular material in contact with the fiber tip.

The sensor layer 82 can be used to provide an indication of temperature and/or pressure if it is desired to control the amount of heat build-up due to the rate of ablation from the tooth 72. In operation, if the temperature or pressure goes above a preselected amount, this would trigger a feedback signal to reduce the repetition rate of the laser pulses and/or the energy/pulse. Further, the fiber 74 can be used to couple radiation of different wavelengths back to the detector 76. The wavelength being detected will depend on how the system is designed, i.e., what type of signature the system is attempting to locate and detect.

While separate fibers 68 and 74 have been illustrated, it will be appreciated that a single fiber or fiber bundles can be used. Also, a bifurcated fiber can be used in which the fiber is split so that the excitation radiation is transmitted through one portion while the return signal is collected through another portion.

The detector 76 is designed to be sensitive to the signature of the species being detected. It can be chosen to be responsive to wavelength, intensity, etc. Suitable detectors include various diodes and diode arrays, charge coupled devices, photomultiplier tubes, etc.

U.S. Pat. No. 5,107,516 described a spectroscopic feedback system utilizing two lasers wherein resonance fluorescence radiation is used to provide a feedback signal to control the ablation laser. In the system of that patent, the distinction to be detected is that between material plaque and normal tissue. Additional references generally describing feedback systems for use with lasers in medical applications and dentistry include D. R. Wyman et al., Proceedings of the IEEE, Vol. 80, No. 6, p. 890, June 1992 and German patent DE 40 15066 A1. In contrast with these references, the present invention uses the signatures of sound and/or color jet and/or tissue temperature described herein to control the ablation laser output used for the treatment of dental tissues.

While the invention has been described with respect to particular embodiments, it will be appreciated by those of skill in the art that variations can be made without departing from the spirit of the present invention. It has been taught that there are ablation threshold windows allowing the use of ultraviolet light to do selective hard tissue and soft tissue dental procedures, a feature which has not heretofore been available to dentists. Depending upon the ultraviolet wavelength chosen, slightly different ablation thresholds will exist for the various types of tooth materil including enamel, dentin, and carious decay. However, regardless of the wavelength chosen, these ablation thresholds can be determined by the procedures described herein and illustrated with respect to the plots of FIG. 3–6.

the windows of operation described herein make it possible to selectively do other procedures safely, as for example curing resins for bonding to tooth structures, sterilizing root canals and other surfaces and removing tartar from tooth surfaces.

We claim:

1. An apparatus for performing laser dentistry on a tooth in a patient's mouth, comprising:

a laser system for producing ultraviolet radiation pulses, delivery means for delivering said radiation pulses to said tooth to ablate material therefrom without substantial heat buildup at said tooth, and control means for automatically controlling the energy fluence of said ultraviolet radiation pulses to selected energy fluences in accordance with the type of material being ablated from said tooth, a first selected energy fluence being at least the threshold fluence $F_1$ necessary to ablate enamel at a selected ultraviolet wavelength, and a second selected energy fluence being greater than the threshold fluence $F_2$ necessary to ablate carious material but less than the fluence $F_1$, at said selected ultraviolet wavelength.

2. The apparatus of claim 1, where said control means includes sensor means for detecting the type of tooth material to be ablated and feedback means to provide a signal to said control means, said control means then regulating said laser system to provide ultraviolet radiation pulses having either said first or second selected energy fluence.

3. The apparatus of claim 1, where said control means can control the energy fluence of said ultraviolet radiation pulses to a third selected energy fluence greater than the threshold $F_3$ necessary to ablate dentin but less than the fluence $F_2$.

4. The apparatus of claim 1, where said selected ultraviolet wavelength is in the range of about 185–220 nm.

5. The apparatus of claim 1, where said selected ultraviolet wavelength is in the range of about 300–400 nm.

6. The apparatus of claim 1, including means for automatically changing the energy fluence of said ultraviolet radiation pulses between said first and second selected energy fluences during laser ablation of said teeth.

7. The apparatus of claim 1, including means for automatically changing the repetition rate of said ultraviolet radiation pulses during laser ablation of said tooth.

8. The apparatus of claim 1, including means for sensing the presence of harmful biological material in the patient's mouth and means for automatically decreasing the energy fluence of said ultraviolet radiation pulses to an energy fluence level that is insufficient to ablate material from said tooth.

9. The apparatus of claim 6, where said selected ultraviolet wavelength is in the range 185–220 n or 300–400 nm.

10. The apparatus of claim 1, where said first selected energy fluence is at least about 5.8 J/cm$^2$ and said second selected energy fluence is greater than about 1.36 J/cm$^2$ and less than about 5.8 J/cm$^2$.

11. The apparatus of claim 10, where said selected ultraviolet wavelength is in the range 18.5–220 nm or 300–400 nm.

12. The apparatus of claim 11, where said laser system includes a solid state laser.

13. The apparatus of claim 12, where said delivery means includes an optical fiber for transmitting said ultraviolet radiation pulses to said tooth.

14. The apparatus of claim 13, including a sensor located near the tip of said optical fiber, said sensor producing a signal indicative of the type of material to be ablated from said tooth.

* * * * *